US009051346B2

(12) United States Patent
Pereira

(10) Patent No.: US 9,051,346 B2
(45) Date of Patent: Jun. 9, 2015

(54) PROCESS FOR PREPARING TRIAZOLE-CONTAINING KETOLIDE ANTIBIOTICS

(75) Inventor: David E. Pereira, Apex, NC (US)

(73) Assignee: CEMPRA PHARMACEUTICALS, INC., Chapel Hill, NC (US)

(*) Notice: Subject to any disclaimer, the term of this patent is extended or adjusted under 35 U.S.C. 154(b) by 0 days.

(21) Appl. No.: 13/699,020

(22) PCT Filed: May 20, 2011

(86) PCT No.: PCT/US2011/037330
§ 371 (c)(1),
(2), (4) Date: Nov. 20, 2012

(87) PCT Pub. No.: WO2011/146829
PCT Pub. Date: Nov. 24, 2011

(65) Prior Publication Data
US 2013/0066056 A1   Mar. 14, 2013

Related U.S. Application Data

(60) Provisional application No. 61/346,664, filed on May 20, 2010.

(51) Int. Cl.
C07H 17/08 (2006.01)
(52) U.S. Cl.
CPC ..................................... *C07H 17/08* (2013.01)
(58) Field of Classification Search
CPC .................................. C07H 1/00; C07H 17/08
See application file for complete search history.

(56) References Cited

U.S. PATENT DOCUMENTS

| 1,354,753 | A | 10/1920 | Howard |
| 4,331,803 | A | 5/1982 | Watanabe |
| 4,474,768 | A | 10/1984 | Bright |
| 4,742,049 | A | 5/1988 | Baker |
| 5,444,051 | A | 8/1995 | Agouridas |
| 5,527,780 | A | 6/1996 | Agouridas |
| 5,543,400 | A | 8/1996 | Agouridas |
| 5,635,485 | A | 6/1997 | Agouridas |
| 5,656,607 | A | 8/1997 | Agouridas |
| 5,747,467 | A | 5/1998 | Agouridas |
| 5,760,233 | A | 6/1998 | Agouridas |
| 5,770,579 | A | 6/1998 | Agouridas |
| 5,834,428 | A | 11/1998 | Drucker |
| 5,985,844 | A | 11/1999 | Heck |
| 6,011,142 | A | 1/2000 | Bonnet |
| 6,020,521 | A | 2/2000 | Randolph |
| 6,028,181 | A | 2/2000 | Or |
| 6,096,714 | A | 8/2000 | Agouridas |
| 6,121,432 | A | 9/2000 | Bonnet |
| 6,395,300 | B1 | 5/2002 | Straub et al. |
| 6,395,710 | B1 | 5/2002 | Chu |
| 6,407,074 | B1 | 6/2002 | Bronk |
| 6,407,257 | B1 | 6/2002 | Agouridas et al. |
| 6,420,535 | B1 | 7/2002 | Phan |
| 6,437,106 | B1 | 8/2002 | Stoner |
| 6,440,941 | B1 | 8/2002 | Denis |
| 6,455,505 | B2 | 9/2002 | Agouridas |
| 6,515,116 | B2 | 2/2003 | Suh et al. |
| 6,555,524 | B2 | 4/2003 | Kaneko |
| 6,664,238 | B1 | 12/2003 | Su |
| 6,777,393 | B2 | 8/2004 | Bronk |
| 6,809,188 | B1 | 10/2004 | Suh et al. |
| 6,849,608 | B2 | 2/2005 | Su |
| 6,890,907 | B2 | 5/2005 | Speirs |
| 7,163,924 | B2 | 1/2007 | Burger |
| 7,332,476 | B2 | 2/2008 | Burger |
| 7,375,234 | B2 | 5/2008 | Sharpless |
| 7,419,961 | B2 | 9/2008 | Napoletano |
| 7,601,695 | B2 | 10/2009 | Liang |
| 8,247,394 | B2 | 8/2012 | Fernandes |
| 8,791,080 | B2 | 7/2014 | Fernandes |
| 8,796,232 | B2 | 8/2014 | Fernandes |
| 2002/0028781 | A1 | 3/2002 | Agouridas |
| 2003/0143162 | A1 | 7/2003 | Speirs |
| 2003/0176327 | A1 | 9/2003 | Cassell |
| 2004/0009930 | A1 | 1/2004 | Su |
| 2005/0009764 | A1 | 1/2005 | Burger et al. |
| 2005/0014706 | A1 | 1/2005 | Falzari |
| 2005/0022242 | A1 | 1/2005 | Rosetti |
| 2005/0153905 | A1 | 7/2005 | Burger |
| 2005/0209172 | A1 | 9/2005 | Woo |
| 2005/0222427 | A1 | 10/2005 | Sharpless |
| 2006/0100164 | A1 | 5/2006 | Liang et al. |
| 2006/0264385 | A1 | 11/2006 | Wang |
| 2007/0015719 | A1 | 1/2007 | Jenkins |
| 2007/0167382 | A1 | 7/2007 | Finkelstein |
| 2007/0197518 | A1 | 8/2007 | Johnson |
| 2007/0281894 | A1 | 12/2007 | Gant |
| 2008/0113926 | A1 | 5/2008 | Ivezic |
| 2008/0221048 | A1 | 9/2008 | Woo |
| 2008/0227730 | A1 | 9/2008 | Mutak |
| 2008/0287376 | A1 | 11/2008 | Das |
| 2009/0075916 | A1 | 3/2009 | Upadhyay |
| 2009/0087389 | A1 | 4/2009 | Leonard |
| 2009/0156517 | A1 | 6/2009 | Zhang |
| 2010/0216731 | A1 | 8/2010 | Pereira |
| 2011/0195920 | A1 | 8/2011 | Fernandes |
| 2012/0071429 | A1 | 3/2012 | Duffield |
| 2012/0172323 | A1 | 7/2012 | Fernandes |
| 2013/0018008 | A1 | 1/2013 | Pereira |
| 2013/0164351 | A1 | 6/2013 | Fernandes |
| 2013/0172280 | A1 | 7/2013 | Pereira |
| 2014/0088062 | A1 | 3/2014 | Pereira |

FOREIGN PATENT DOCUMENTS

CN    1354753    6/2002
CN    101045063    10/2007
(Continued)

OTHER PUBLICATIONS

LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.
(Continued)

*Primary Examiner* — Elli Peselev
(74) *Attorney, Agent, or Firm* — Brannon Sowers & Cracraft PC

(57) ABSTRACT

The invention described herein pertains to processes for the preparation of macrolide antibacterial agents. In particular, the invention pertains to processes for preparing macrolides and ketolides from erythromycin A.

35 Claims, No Drawings

(56) References Cited

FOREIGN PATENT DOCUMENTS

| EP | 0248279 A2 | 12/1987 |
|---|---|---|
| EP | 0680967 | 11/1995 |
| EP | 1024145 A2 | 8/2000 |
| EP | 1167375 | 1/2002 |
| JP | 2000507573 | 6/2000 |
| JP | 2000351794 | 12/2000 |
| JP | 2004502736 | 1/2004 |
| JP | 2006528667 | 12/2006 |
| JP | 2007536371 | 12/2007 |
| JP | 2008519788 | 6/2008 |
| WO | 9830574 A1 | 7/1998 |
| WO | 9856800 | 12/1998 |
| WO | 9921866 A1 | 5/1999 |
| WO | 9928311 A1 | 6/1999 |
| WO | 0012521 A1 | 3/2000 |
| WO | 0031099 | 6/2000 |
| WO | 0031099 A1 | 6/2000 |
| WO | 0044761 A2 | 8/2000 |
| WO | 0062783 A2 | 10/2000 |
| WO | 0110878 | 2/2001 |
| WO | 0250092 A1 | 6/2002 |
| WO | 03004509 A2 | 1/2003 |
| WO | WO03004509 | 1/2003 |
| WO | 03072141 A1 | 9/2003 |
| WO | WO2004080391 | 9/2004 |
| WO | 2005105821 | 11/2005 |
| WO | 2006087642 | 8/2006 |
| WO | 2007008537 | 1/2007 |
| WO | 2007059307 | 5/2007 |
| WO | 2007143507 | 12/2007 |
| WO | 2009055557 | 4/2009 |
| WO | WO2009055557 | 4/2009 |
| WO | 2011008193 | 1/2011 |
| WO | 2011112864 A1 | 9/2011 |
| WO | WO2011119604 | 9/2011 |
| WO | 2011146829 | 11/2011 |
| WO | 2013148891 | 10/2013 |
| WO | 2014145210 | 9/2014 |
| WO | 2014152326 | 9/2014 |

OTHER PUBLICATIONS

Romero et al., 'An efficient entry to new sugar modified ketolide antibiotics' Tetrahedron Letters, vol. 46, 2005, pp. 1483-1487.
Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.
Vince, R., Almquist, R. G., Ritter, C. L., and Deluge, S., Antimicrobial Agents and Chemotherapy, vol. 8, No. 4, 1975, 439-443.
Or et al., 'Design, Synthesis, and Antimicrobial Activity of 6-0-Substituted Ketolides Active Against Resistant Respiratory Tract Pathogens', J. Med. Chem., 43:1045-49 (2000).
Champney et al., 'Structure-Activity Relationships for Six Ketolide Antibiotics', Current Microbiology, 42:203-10 (2001).
Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).
Torne et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 37:3057-64 (2002).
Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).
Baker, W.R. et al., 'Modification of macrolide antibiotics. Synthesis of 11-deoxy-11-(carboxyamino)-6-0-methylerythromycin A 11,12-(cyclic esters) via an intramolecular Michael reaction of O-carbamates with an alpha, Beta-unsaturated ketone,' J. Org. Chem., 53:2340-2345, 1988.

Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).
Phan, L.T. et al., 'Synthesis of 2-Fluoro-6-O-propargyl-11,12-carbamate Ketolides. A Novel Class of Antibiotics,' Org. Ltrs., 2:2951-2954 (2000).
Liang C. H. et al., 'Synthesis and biological activity of new 5-0-sugar modified ketolide and 2-fluoro-ketolide antibiotics,' Bioorganic & Medicinal Chemistry Letters, Pergamon, Elsevier Science, GB, vol. 15, No. 5, Mar. 1, 2005, pp. 1307-1310.
Plata et al., "The synthesis of ketolide antibiotic ABT-773 (cethromycin)," Tetrahedron, vol. 60, 2004, pp. 10171-10180.
Ma et al., Curr. Med. Chem., "Anti-Infective Agents," vol. 1, 2002, pp. 15-34.
Holzer, G., et al., "Ka1,2 and KB1,3 X-Ray Emission Lines of the 3d Transition Metals", Dec. 1997, Physical Review, vol. 56, No. 6, pp. 4554-4568.
Jones et al.: 'MIC Quality Control Guidelines and Disk Diffusion Test Optimization for CEM-101, a Novel Fluoroketolide' Journal of Clinical Microbiology vol. 48, No. 4, Dec. 30, 2009, pp. 1470-1473.
Berge, Stephen M., et al., "Pharmaceutical Salts", 1977, Journal of Pharmaceutical Sciences, vol. 66, No. 1, pp. 1-19.
Bermudez, Luiz E., et al., "Telithromycin is Active Against Mycobacterium Avium in Mice Despite Lacking Significant Activity in Standard In Vitro and Macrophage Assays and Is Associated with Low Frequency of Resistance During Treatment", 2001, Antimicrobal Agents and Chemotherapy, vol. 45, No. 8, pp. 2210-2214.
Bermudez, Luiz E., et al., "EDP-420, a Bicyclolide (Bridged Bicyclic Macrolide), Is Active Against Mcyobacterium Avium", 2007, Antimicrobal Agents and Chemotherapy, vol. 51, No. 5, pp. 1666-1670.
Cynamon, M. H., et al., "Activity of ABT-773 Against Mycobacterium Avium Complex in the Beige Mouse Model", 2000, Antimicrobal Agents and Chemotherapy, vol. 44, No. 10, pp. 2895-2896.
Patel, Ramesh N., "Stereoselective Biocatalysis", 2000, Bristol-Myers Squibb Research Institute; pp. 775-797.
Vennerstrom, Jonathan L., et al., "Identification of an Antimalarial Synthetic Trioxolane Drug Development Candidate", 2004, Letters to Nature, vol. 430, pp. 900-904.
Barcia-Macay, Maritza, et al., 'Pharmacodynamic Evaluation of the Intracellular Activities of Antibiotics Against Staphylococcus aureus in a Model of THP-1 Macrophages', 2006, Antimicrobial Agents and Chemotherapy. vol. 50, No. 3, pp. 841-851.
Bebear, C.M., et al., In vitro activity of trovafloxacin compared to those of five antimicrobials against mycoplasmas including Mycoplasma hominis and Ureaplasma urealyticum fluoroquinolone-resistant isolates that have been genetically characterized, Antimicrob Agents Chemother 44:2557-2560 (2000).
Duffy, L. et al., Fluoroquinolone resistance in Ureaplasma parvum in the United States, J Clin Microbiol 44:1590-1591 (2006).
Waites, K.B., et al., Mycoplasmas and ureaplasmas as neonatal pathogens, Clin Microbiol Rev 18:757-89 (2005).
Zuckerman, "Macrolides and ketolides: azithromycin, clarithromycin, telithromycin", Infectious Disease Clinics of North America, vol. 18, (2004), pp. 621-649.
Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp. 799, 800.
Laine, Loren, et al., "Prospective comparison of H&E, Giemsa and Genta stains or the diagnosis of Helicobacter pylori," 1997, Gastrointestinal Endoscopy, vol. 45, No. 6, pp. 463-467.
Lee, Adrian, et al., "A standard mouse model of Helicobacter pylori infection: introducing the Sydney Strain," 1997, Gastroenterology, vol. 112, pp. 1386-1397.
Drusano, G. L., et al., "Is 60 Days of Ciprofloxacin Adminstration Necessary for Postexposure Prophylaxis for Bacillus anthracis?", 2008, Antimicrobial Agents and Chemotherapy. vol. 52, No. 11, pp. 3973-3979.
Feder, P. I., et al., 1991. Statistical Analysis of Dose-Response Experiments by Maximum Likelihood Analysis and Iteratively

(56) References Cited

OTHER PUBLICATIONS

Reweighted Nonlinear Least Squares Regression Techniques, 1991, Drug Information Journal, vol. 28, pp. 323-334.
Inglesby, Thomas V., et al., "Anthrax as a Biological Weapon, 2002", 2002, Journal of the American Medical Association, vol. 287, No. 17, pp. 2236-2252.
Celebuski, J.E. et al., 'Chemical Modification of Erythromycin: Novel Reaction observed by Treatment with Metalloporphyrins', vol. 35, No. 23, pp. 3837-3850, 994, Elsevier Science Ltd.
Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.
Hill, D.R. et al., 'Novel Macrolides via meso-Tetraarylmetalloporphyrin Assisted oxidation', Tetrahedron Letters, vol. 37, No. 6, pp. 787-790, 1996, Elsevier Science Ltd.
Physicians' Desk Reference, p. 2905, (2007).
Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.
Jensen, J.S., et al., Azithromycin Treatment Failure in *Mycoplasma genitalium*Positive Patients with Nongonococcal Urethritis Is Associated with Induced Macrolide Resistance, Clin Infect Dis 47:1546-53 (2008).
Li, X., et al., Emerging macrolide resistance in *Mycoplasma pneumoniae* in children: detection and characterization of resistant isolates, Pediatr Infect Dis J, 28:693-696 (2009).
Lemaire, Sandrine, et al., "Cellular Accumulation and Pharmacodynamic Evaluation of the Intracellular Activity of CEM-101, a Novel Fluoroketolide, Against *Staphylococcus aureus*, *Listeria Monocytogenes* and *Legionella pneumophila* in Human THP-1 Macrophages", 2009, Antimicrobial Agents and Chemotherapy. vol. 53, No. 9, pp. 3734-3743.
PCT International Search Report and Written Opinion for PCT/US2011/029424, mailed May 25, 2011.
PCT Search Report and Written Opinion for PCT/US2011/037330 completed Aug. 26, 2011.
Caira MR, "Crystalline polymorphism of orgainic compounds," Design of Organic Solids, Topics in Current Chemistry, Springer Berlin Heidelberg, 1998, p. 163-208.
Pathak et al., "Enzymatic Protecting Group Techniques in Organic Synthesis," Stereosel, Biocatal., 2000; pp. 775-797.
Katz, Leonard, and Gary W. Ashley. "Translation and protein synthesis: macrolides." Chemical reviews 105.2 (2005): 499-528.
Threlfall, Terence L. "Analysis of organic polymorphs. A review." Analyst 120.10 (1995): 2435-2460.
Petit, Samuel, and Gérard Coquerel. "The amorphous state." Polymorphism: In the Pharmaceutical Industry 10 (2006): 1.

Organic Compounds Crystal Manufacture Handbook—Principles and Knowhow, 2008, pp. 57 to 84.
Hancock, Bruno C., Sheri L. Shamblin, and George Zografi. "Molecular mobility of amorphous pharmaceutical solids below their glass transition temperatures." Pharmaceutical research 12.6 (1995): 799-806.
Ashizawa, Kazuhide, "Physico-Chemical Studies on the molecular Details of Drug Crystals," Phar Tech Japan, 2002, vol. 18, No. 10. pp. 81-96.
PCT Search Report and Written Opinion prepared for PCT/US2009/061978 mailed Dec. 9, 2009.
European Search Report for EP 09 82 2827, dated Mar. 21, 2012.
International Search Report for PCT/US2009/061977, dated Dec. 23, 2009, (3 pages).
PCT Search Report/Written Opinion prepared for PCT/US2010/048540, mailed Oct. 21, 2010.
Byrn, S., Pfeiffer, R., Ganey, M., Hoiberg, C., & Poochikian, G. (1995). Pharmaceutical solids: a strategic approach to regulatory considerations. Pharmaceutical research, 12(7), 945-954.
Sumerkan, B., Aygen, B., Doganay, M., & Sehmen, E. (1996). Antimicrobial susceptibility of *Bacillus anthracis* against macrolides. Salisbury Med Bull Supplement, 87, 138.
Maurin, M., Mersali, N. F., & Raoult, D. (2000). Bactericidal activities of antibiotics against intracellular *Francisella tularensis*. Antimicrobial agents and chemotherapy, 44(12), 3428-3431.
Luna, V. A., King, D. S., Gulledge, J., Cannons, A. C., Amuso, P. T., & Cattani, J. (2007). Susceptibility of *Bacillus anthracis, Bacillus cereus, Bacillus mycoides, Bacillus pseudomycoides* and *Bacillus thuringiensis* to 24 antimicrobials using Sensititre® automated microbroth dilution and Etest® agar gradient diffusion methods. Journal of antimicrobial chemotherapy, 60(3), 555-567.
Barthel, D., Schlitzer, M., & Pradel, G. (2008). Telithromycin and quinupristin-dalfopristin induce delayed death in *Plasmodium falciparum*. Antimicrobial agents and chemotherapy, 52(2), 774-777.
Still, J. G., et al. "Single Oral Dose Pharmacokinetics and Safety of CEM-101 in Healthy Subjects." 46th Annual Meeting. Idsa, 2008.
Lee, Joo Hyun, and Myung Gull Lee. "Dose-dependent pharmacokinetics of telithromycin after intravenous and oral administration to rats: contribution of intestinal first-pass effect to low bioavailability." J. Pharm. Pharm. Sci 10 (2007): 37-50.
Chen, M., Muri, E. M., Jacob, T. M., & Williamson, J. S. (2003). Synthesis and bioactivity of erythromycin derivatives. Medicinal chemistry research, 12(3), 111-129.
Kerdesky, F. A., Premchandran, R., Wayne, G. S., Chang, S. J., Pease, J. P., Bhagavatula, L., . . . & King, S. A. (2002). Synthesis of 2'-O-Benzoyl-3-keto-6-O-propargyl-11, 12-carbamoyl Erythromycin A. Organic process research & development, 6(6), 869-875.
Zhu, Z. J., Krasnykh, O., Pan, D., Petukhova, V., Yu, G., Liu, Y., . . . & Franzblau, S. G. (2008). Structure-activity relationships of macrolides against *Mycobacterium tuberculosis*. Tuberculosis, 88, S49-S63.
International Search Report Written Opinion for PCT/US2008/080936 completed Dec. 8, 2008.

PROCESS FOR PREPARING TRIAZOLE-CONTAINING KETOLIDE ANTIBIOTICS

CROSS-REFERENCE TO RELATED APPLICATIONS

This application is a U.S. national application under 37 C.F.R. §371(b) of International Application Serial No. PCT/US2011/037330 filed May 20, 2011, which claims the benefit of U.S. provisional application 61/346,664, filed 20 May 2010, the disclosures of which are incorporated by reference herein.

TECHNICAL FIELD

The invention described herein pertains to processes for the preparation of macrolide antibacterial agents. In particular, the invention pertains to processes for preparing macrolides and ketolides from erythromycin A.

BACKGROUND AND SUMMARY OF THE INVENTION

Macrolide antibiotics, characterized by a large lactone ring to which are attached one or more deoxy sugars, usually cladinose and desosamine, are antimicrobial drugs that are active against aerobic and anaerobic gram positive cocci and are prescribed for the treatment of respiratory tract and soft tissue infections. The macrolides, which belong to the polyketide class of natural products, function by reversibly binding to the 50S subunit of the bacterial ribosome, blocking protein synthesis and preventing bacterial growth and reproduction. Although this action is primarily bacteriostatic, at higher concentrations, macrolides can be bactericidal. Erythromycin and the semi-synthetic derivatives azithromycin and clarithromycin are among the marketed macrolide antibiotics.

Ketolides, which are semi-synthetic derivatives of the 14-membered macrolide erythromycin A, belong to this class of drugs used to treat respiratory tract infections. These drugs are effective against macrolide-resistant bacteria because of their ability to bind to two sites on the bacterial ribosome. Telithromycin and cethromycin belong to this group of antibiotics.

Acquired bacterial resistance to macrolides occurs primarily through post-transcriptional methylation of the 23S bacterial ribosome. This results in cross-resistance to macrolides, lincosamides and streptogramins. Although rare, acquired resistance also can result from the production of drug-inactivating enzymes such as esterases or kinases, as well as the production of active ATP-dependent efflux proteins that transport macrolides out of the cell. A significant fraction of pneumococci are resistant to currently available antibiotics. Accordingly, new macrolide and ketolide antibiotics are needed, along with processes for preparing them.

In particular, international patent application publication No. WO 2004/080391, and its counterpart publication US 2006/0100164, the disclosures of which are incorporated herein by reference, describes a family of macrolide andketolide antibiotics, including fluoroketolide antibiotics, of formula (I)

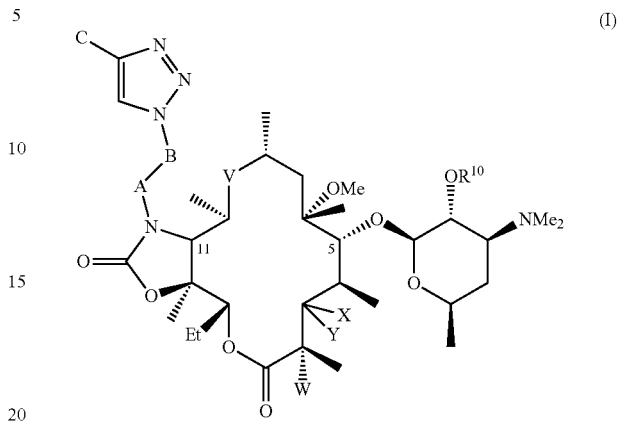

and pharmaceutically acceptable salts thereof, wherein $R^{10}$, X, Y, V, W, A, B, and C are as described herein, and Me indicates methyl, and Et indicates ethyl. One notable, but non-limiting example compound of formula (I) is solithromycin, also referred to as OP-1068 and/or CEM-101. The preparation of CEM-101 and related compounds is described in WO 2009/055557, the disclosure of which is incorporated herein by reference. A starting material used in WO 2009/055557 A1 for the preparation of the macrolide antibacterial agents is clarithromycin. In the processes described therein, clarithromycin is converted into a clarithromycin derivative in which the hydroxyl groups of the sugar moieties are protected with acyl groups, such as clarithromycin dibenzoate, also known as 2',4"-di-O-benzoyl-6-O-methylerythromycin A, to form compounds of formula (II).

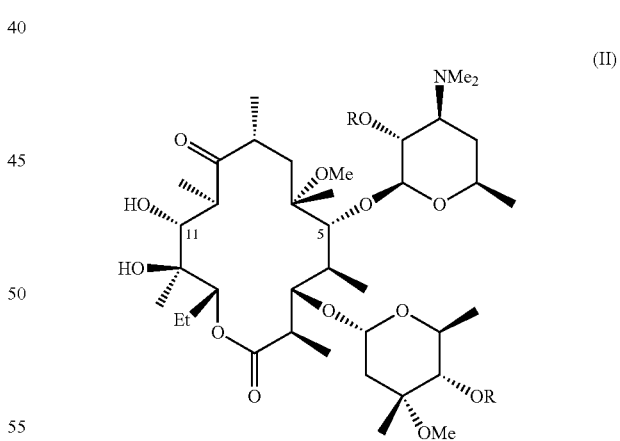

and pharmaceutically acceptable salts thereof, wherein R is as described herein.

Clarithromycin is a semisynthetic antibacterial agent in which the 6-hydroxy group of erythromycin A has been converted into a 6-methoxy group to eliminate undesired interaction with the carbonyl group at the 9-position of the macrolide ring, thereby stabilizing the antibiotic. Clarithromycin has been prepared by various processes. The most widely used processes begin with erythromycin A, which is converted to its oxime and then to a protected erythromycin A 9-oxime derivative as an intermediate, and variously involve protection and deprotection of the hydroxyl and dimethyl groups of the pendant sugar moieties before and after methylation of the 6-hydroxy group of the macrolide ring (see, for example, U.S. Pat. No. 6,515,116 for a review of the reported processes; an alternative approach including protection of the desosaminyl amino group as an N-oxide is described in U.S. Pat. No. 6,809,188). For the efficient production of a clarithromycin derivative in which the hydroxyl groups of the sugar moieties are protected with acyl groups and, subsequently, of a final macrolide antibacterial agent, there is needed a preparation of the diprotected derivative from erythromycin A which avoids the protecting and deprotecting steps used in the prior methodology for the preparation of clarithromycin. Described herein are processes for the direct production from erythromycin A of clarithromycin derivatives of formula (II) in which the hydroxyl groups of the sugar moieties are protected with acyl groups with a reduced number of steps. Also described herein are processes for preparing compounds of formula (I) from compounds of formula (II).

DETAILED DESCRIPTION

In one illustrative embodiment of the invention, processes are described for preparing compounds of formula (I)

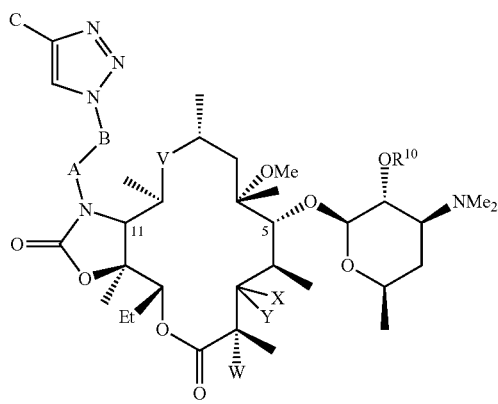

(I)

and pharmaceutically acceptable salts thereof, wherein:

$R^{10}$ is hydrogen, acyl or a prodrug moiety;

X is H; and Y is $OR^7$; where $R^7$ is monosaccharide, disaccharide, alkyl, arylalkyl, or heteroarylalkyl, each of which is optionally substituted, or acyl or $C(O)NR^8R^9$; where $R^8$ and $R^9$ are each independently selected from the group consisting of hydrogen, hydroxy, alkyl, heteroalkyl, alkoxy, aryl, arylalkyl, heteroaryl, and heteroarylalkyl, each of which is optionally substituted, and dimethylaminoalkyl, acyl, sulfonyl, ureido, and carbamoyl; or $R_8$ and $R_9$ are taken together with the attached nitrogen to form an optionally substituted heterocycle; or X and Y are taken together with the attached carbon to form carbonyl;

V is C(O), C(=$NR^{11}$), CH($NR^{12}$, $R^{13}$), or N($R^{14}$)CH$_2$; where N($R^{14}$) is attached to the C-10 carbon; where $R^{11}$ is hydroxy or alkoxy; $R^{12}$ and $R^{13}$ are each independently selected from the group consisting of hydrogen, hydroxy, alkyl, alkoxy, heteroalkyl, aryl, arylalkyl, heteroaryl, and heteroarylalkyl, each of which is optionally substituted, and dimethylaminoalkyl, acyl, sulfonyl, ureido, and carbamoyl; $R^{14}$ is hydrogen, hydroxy, alkyl, alkoxy, heteroalkyl, aryl, arylalkyl, heteroaryl, or heteroarylalkyl, each of which is optionally substituted, or dimethylaminoalkyl, acyl, sulfonyl, ureido, or carbamoyl;

W is H, F, Cl, Br, I, or OH;

A is CH$_2$, C(O), C(O)O, C(O)NH, S(O)$_2$, S(O)$_2$NH, or C(O)NHS(O)$_2$;

B is (CH$_2$)$_n$ where n is an integer from 0 to 10; or an unsaturated carbon chain of 2 to 10 carbons; and C is hydrogen, hydroxy, alkyl, alkoxy, heteroalkyl, aryl, arylalkyl, heteroaryl, or heteroarylalkyl, each of which is optionally substituted, or acyl, acyloxy, sulfonyl, ureido, or carbamoyl.

In another illustrative embodiment, processes are described for preparing compounds of formula (II)

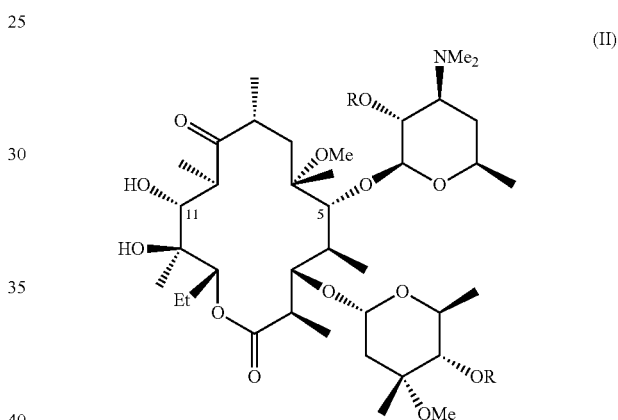

(II)

and pharmaceutically acceptable salts thereof, wherein R is an acyl group. In another embodiment, R is a hindered acyl group, such as benzoyl.

In another embodiment, processes are described herein comprising the step of (a) contacting a compound of formula (III)

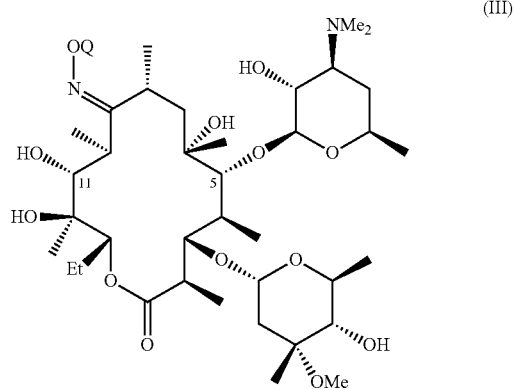

(III)

or an acid addition salt thereof, with an acylating agent to prepare a compound of formula (IV)

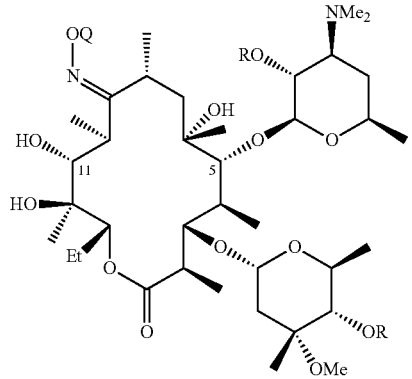

or an acid addition salt thereof; where in each instance Q in combination with the oxime oxygen forms an acetal or a ketal, or Q is tropyl, and R is an acyl group. In another embodiment, the step (a) of the processes includes a base.

In another illustrative embodiment, processes are described herein comprising the step of (b) contacting a compound of formula (IV), as described herein, or an acid addition salt thereof, with a methylating agent to prepare a compound of formula (V)

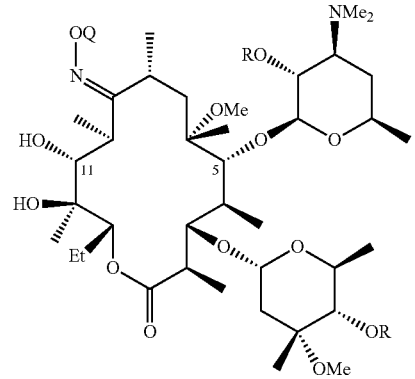

or an acid addition salt thereof, where Q and R are as described in the alternative embodiments herein. In another embodiment, the step (b) of the processes includes a base. In another embodiment, the step (b) of the processes includes an aprotic polar solvent.

In another illustrative embodiment, processes are described herein comprising the step of (c) contacting a compound of formula (V), as described herein, or an acid addition salt thereof, with a deoximating agent to form the compound of formula (II),

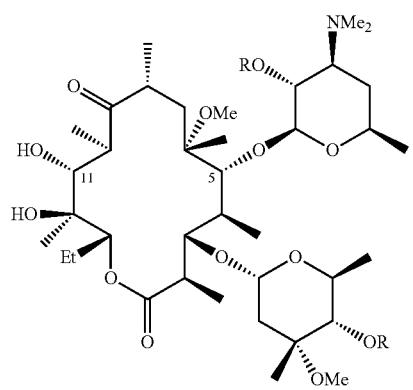

or an acid addition salt thereof, where R is described in the alternative embodiments herein.

It is to be understood that each of the steps (a), (b), and (c) may be combined in additional embodiments. It is further to be understood that the variations of each of the steps (a), (b), and (c) described herein may be combined without limitation in additional embodiments. For example, another illustrative process comprises acylating step (a) and further comprises methylating step (b), and further comprises deoximating step (c). Another illustrative process comprises methylating step (b) and further comprises deoximating step (c). Another illustrative process comprises acylating step (a) and further comprises methylating step (b), and further comprises deoximating step (c), and further comprises steps described in WO 2009/055557 for converting compounds of formula (II) into compounds of formula (I).

In another embodiment, processes for preparing compounds of formula (IV), such as compounds of formula (IV) where R is benzoyl, or an acid addition salt thereof, are described herein, where the processes comprise the step of contacting a compound of formula (III), as described herein, or an acid addition salt thereof, with an acylating agent, such as benzoyl anhydride, also referred to as benzoic anhydride, to form a compound of formula (IV), or an acid addition salt thereof. In one variation, the step is performed in the presence of a base.

In another embodiment, processes for preparing compounds of formula (V), or an acid addition salt thereof, as described herein, where the processes comprise the step of contacting a compound of formula (IV), as described herein, or an acid addition salt thereof, with a methylating agent, to form a 6-O-methyl compound of formula (V), as described herein, or an acid addition salt thereof. In one variation, the step is performed in the presence of a base. In another variation, the step is performed in an aprotic polar solvent. In another variation, the step is performed in the presence of a base and in an aprotic polar solvent.

In another embodiment, processes for preparing compounds of formula (II), including compounds of formula (II) where R is benzoyl, or an acid addition salt of any of the foregoing, are described herein, where the processes comprise the step of contacting a compound of formula (V), as described herein, or an acid addition salt thereof, with a deoximating agent to form a compound of formula (II), or an acid addition salt thereof.

In another illustrative embodiment of any of the foregoing processes, Q is an O-protecting group. In one variation, Q in combination with the oxime oxygen forms an acetal or ketal, or Q is tropyl. In another illustrative embodiment, R is an acyl group. In another illustrative embodiment, Q is an O-protecting group. In one variation, Q in combination with the oxime oxygen forms an acetal or ketal, or Q is tropyl, and R is an acyl group.

In another illustrative embodiment of any of the foregoing processes, Q is $C(R^A)(R^C)(OR^B)$, wherein $R^A$ is a group of the formula $CH_2R^D$, where $R^D$ is hydrogen, (1-3C)alkyl or (1-6C)alkoxy;

$R^B$ is (1-6C)alkyl, (5-7C)cycloalkyl; phenyl or arylalkyl; and $R^C$ is hydrogen, (1-4C)alkyl, phenyl or arylalkyl; or alternatively in any of the foregoing $R^B$ and $R^D$ together form an ethylene, propylene or trimethylene group; or $R^B$ and $R^D$ together form a (3-5C)alkanediyl group which may be further substituted with one to three (1-3C)alkyl substituents; or $R^B$ and $R^C$ together form a (3-4C)alkanediyl group.

In another embodiment of any of the foregoing processes, Q is 2-methoxy-2-propyl, 1-methoxycyclohexyl, or 1-isopropoxycyclohexyl. In another embodiment of any of the foregoing processes, Q is 2-methoxy-2-propyl.

Compounds of formula (III), as described herein, may be prepared by contacting erythromycin A 9-oxime with a corresponding compound of formula $R^E—C(R^A)(R^C)(OR^B)$ in which $R^E$ is (1-6C)alkoxy or in which $R^A$ and $R^E$ together form a group of formula $CHR^D$ connected by a double bond. The step may be carried out in the presence of an acidic catalyst, for example in the presence of pyridine hydrochloride. In another variation, the step is performed using 2-methoxypropene to form a compound of formula (III) in which Q is 2-methoxy-2-propyl. In another variation, the step is performed, in dichloromethane at about 0° C. to about room temperature in the presence of pyridine hydrochloride using excess 2-methoxypropene. In another variation, Q is tropyl, and the compounds of formula (III) may be prepared by reacting erythromycin A 9-oxime with tropylium tetrafluoroborate in an aprotic polar solvent.

In another embodiment of any of the processes described herein, R is a sterically hindered acyl group, such as a benzoyl group. In another embodiment of any of the processes described herein, R is not acetyl. Without being bound by theory, it is believed herein that the use of a sterically hindered group R may improve the processes and/or the purity of the isolated product of the processes. It has been discovered that unhindered acyl groups, such as acetyl groups, present on the C-5 saccharide may migrate to other positions on the macrolide, for example from the 2'-hydroxy group of the desosamine moiety to an amino group of a side chain. Use of a sterically hindered group R decreases and/or precludes such a migration leading to improved processes and/or improved purities of the isolated product of the processes In another embodiment of any of the processes described herein, R is benzoyl.

In another embodiment of any of the processes described herein, step (a) is performed with an acylating agent is the anhydride, acid halide, or an activated ester of the corresponding acyl group R. In another embodiment of any of the processes described herein, the acylating agent is the anhydride of the acyl group R. In another embodiment of any of the processes described herein, about 2 to about 6 equivalents of acylating agent to an equivalent of the compound of formula (III) is employed. In another embodiment of any of the processes described herein, a base is included in step (a), such as a tertiary amine. In another embodiment of any of the processes described herein, the base is triethylamine, diisopropylethylamine, or 4-methylmorpholine, or a combination thereof. In another embodiment of any of the processes described herein, about 1 to about 4 equivalents of base to an equivalent of the compound of formula of formula (III) is employed. In another embodiment of any of the processes described herein, the acylation is performed in the presence of about 0.5 to about 2.5 equivalents of an acylation catalyst to an equivalent of the compound of formula of formula (III). In another embodiment of any of the processes described herein, the acylation catalyst is 4-dimethylaminopyridine.

In another embodiment of any of the processes described herein, the methylating agent is methyl bromide, methyl iodide, dimethyl sulfate, methyl p-toluenesulfonate, or methyl methanesulfonate. In another embodiment, the methylating agent is methyl iodide. In another embodiment of a process described herein, a base is used in combination with the methylating agent, such as sodium hydroxide, potassium hydroxide, sodium hydride, potassium hydride, or potassium t-butoxide, or a mixture thereof. In another embodiment the base used with the methylating agent is potassium hydroxide. In another embodiment the methylation step is performed in an aprotic polar solvent, such as dimethyl sulfoxide, dimethylformamide, 1-methyl-2-pyrrolidone, a mixture thereof, or a mixture of any of these solvents with one or more of tetrahydrofuran, 2-methyltetrahydrofuran, 1,2-dimethoxyethane, acetonitrile or ethyl acetate. In another embodiment of any of the processes described herein, the methylating step is performed at a temperature from about −15° C. to about 60° C. Another embodiment of processes described herein for the methylation of a compound of formula (IV) is one wherein the methylating step is performed at a temperature from about 0° C. to about 30° C.

It has been unexpectedly discovered herein that the methylation step of compounds of formula (IV), where R is benzoyl, is performed without, any or substantially any, cleavage of the benzoate ester present on compounds of formula (IV).

Illustratively, removal of the group Q, such as by O-deprotection, and/or removal of the oxime group at C-9 to form a ketone, such as by deoximation, may be performed using any of a number of conventional processes and/or reagents. Illustrative deoximation methods include, but are not limited to, hydrolytic, oxidative and reductive conditions. In one embodiment, the deoximating agent comprises a reducing agent. Illustrative embodiments of deoximating agents include, but are not limited to, inorganic sulfur oxide compounds such as sodium hydrogen sulfite, sodium pyrosulfate, sodium thiosulfate, sodium sulfite, sodium hydrosulfite, sodium metabisulfite, sodium bisulfite, sodium dithionate, potassium hydrogen sulfite, potassium thiosulfate and potassium metabisulfite, and mixtures thereof. In another embodiment of any of the processes described herein, the deoximating agent is sodium metabisulfite or sodium bisulfite, or a combination thereof. It is to be understood that O-deprotection may be performed prior to deoximation; or O-deprotection and deoximation may be performed in a single ("one-pot") step by treatment, either sequentially, concurrently, contemporaneously, or simultaneously by using acid, such as formic acid, and a deoximating agent.

In another embodiment of any of the processes described herein, the step of converting the C-9 oxime into a carbonyl is performed by contacting the compound of formula (V) wherein the deoximating agent comprises formic acid and sodium metabisulfite in an aqueous alcoholic solution at a temperature ranging from ambient temperature to about the boiling point of the solvent.

It has been unexpectedly discovered that removing the O-protecting group Q and removing the oxime from a compound of formula (V) in which R is benzoyl may be performed without, any or substantially any, cleavage of the benzoate ester present on compounds of formula (V).

It is to be understood that the various subgenera, species, and compounds described herein may be made by the various embodiments of the processes described herein. For example, in another embodiment of any of the processes herein, V is C(O); and/or $R^7$ is an aminosugar or a halosugar; or $R^7$ is 4-nitro-phenylacetyl or 2-pyridylacetyl; or X and Y are taken together with the attached carbon to form carbonyl; and/or A is $CH_2$; and/or B is alkenylene; and/or B is $(CH_2)_n$; where n is 2 to 6, 2 to 5, or 2 to 4, or 2 to 3, or 3; and/or C is aminophenyl; or C is 3-aminophenyl; and/or W is fluoro; or W is hydrogen; and/or $R^{10}$ is hydrogen or acyl; or $R^{10}$ is hydrogen; or $R^{10}$ is benzoyl.

In another embodiment of any of the processes described herein, the compound of formula (I) is CEM-101, or a pharmaceutically acceptable salt, solvate or hydrate thereof. The compound CEM-101 has Chemical Abstracts Registry Number 760981-83-7, and structure of the compound is as follows:

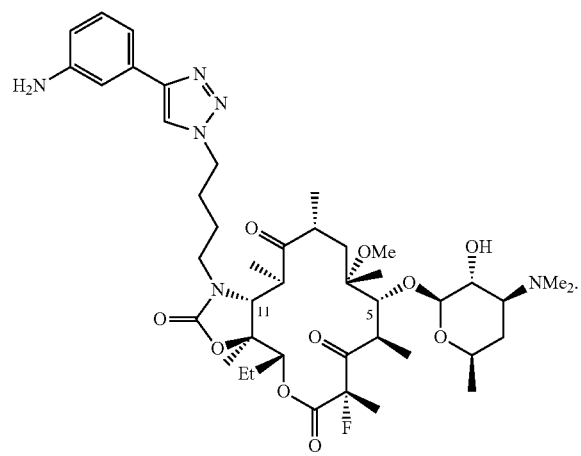 [SMILES: CC[C@H]1OC(=O)[C@@](C)(F)C(=O)[C@H](C)[C@@H](O[C@@H]2O[C@H](C)C[C@H](N(C)C)[C@H]2O)[C@@](C)(OC)C[C@@H](C)C(=O)[C@H](C)[C@H]2N(CCCCn3cc(-c4cccc(N)c4)nn3)C(=O)O[C@]12C]

As used herein, the term "alkyl", alone or in combination, refers to an optionally substituted straight-chain, optionally substituted branched-chain, or optionally substituted cyclic alkyl radical having from 1 to about 30 carbons, more preferably 1 to 12 carbons. Examples of alkyl radicals include methyl, ethyl, n-propyl, isopropyl, n-butyl, isobutyl, sec-butyl, tert-butyl, tert-amyl, pentyl, hexyl, heptyl, octyl and the like. A "lower alkyl" is a shorter alkyl, e.g., one containing from 1 to about 6 carbon atoms.

The term "alkoxy," alone or in combination, refers to an alkyl ether radical, alkyl-O, wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "alkenyl," alone or in combination, refers to an optionally substituted straight-chain, optionally substituted branched-chain, or optionally substituted cyclic alkenyl hydrocarbon radical having one or more carbon-carbon double-bonds and having from 2 to about 30 carbon atoms, more preferably 2 to about 18 carbons. Examples of alkenyl radicals include ethenyl, propenyl, butenyl, 1,4-butadienyl and the like. The term can also embrace cyclic alkenyl structures. A "lower akenyl" refers to an alkenyl having from 2 to about 6 carbons.

The term "acyloxy" refers to the ester group OC(O)—R, where R is H, alkyl, alkenyl, alkynyl, aryl, or arylalkyl, wherein the alkyl, alkenyl, alkynyl and arylalkyl groups may be optionally substituted.

The term "acyl" includes alkyl, aryl, heteroaryl, arylalkyl or heteroarylalkyl substituents attached to a compound via a carbonyl functionality (e.g., CO-alkyl, CO-aryl, CO-arylalkyl or CO-heteroarylalkyl, etc.).

The term "heteroalkyl" generally refers to a chain of atoms that includes both carbon and at least one heteroatom. Illustrative heteroatoms include nitrogen, oxygen, and sulfur.

As used herein, the term "aryl" includes monocyclic and polycyclic aromatic carbocyclic and aromatic heterocyclic groups, each of which may be optionally substituted. As used herein, the term "heteroaryl" includes aromatic heterocyclic groups, each of which may be optionally substituted. Illustrative carbocyclic aromatic groups described herein include, but are not limited to, phenyl, naphthyl, and the like. Illustrative heterocyclic aromatic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

The term "arylalkyl" refers to an alkyl group substituted with one or more unsubstituted or substituted monocyclic or polycyclic aryl groups. Illustrative arylalkyl groups include benzyl, diphenylmethyl, trityl, 2-phenylethyl, 1-phenylethyl, 2-pyridylmethyl, 4,4'-dimethoxytrityl, and the like.

The term "alkylaryl" refers to an aryl group substituted with an alkyl group.

The term "sulfonyl" refers to $SO_2$—R where R is H, alkyl or aryl.

The term "saccharide" includes monosaccharides, disaccharides, and polysaccharides, each of which is optionally substituted. The term also includes sugars and deoxysugars optionally substituted with amino, amido, ureyl, halogen, nitrile, or azido groups. Illustrative examples include, glucosamine, N-acetylglucosamine, desosamine, forosamine, sialic acid, and the like.

The term "activated ester" includes carboxylic acid derivatives in which the hydrogen of the hydroxy group has been replaced with a residue which results in the formation of a good leaving group, including the 4-nitrophenyl ester and an activated ester or anhydride derived from a coupling reagent.

In another embodiment, compounds of formula (IV) are described

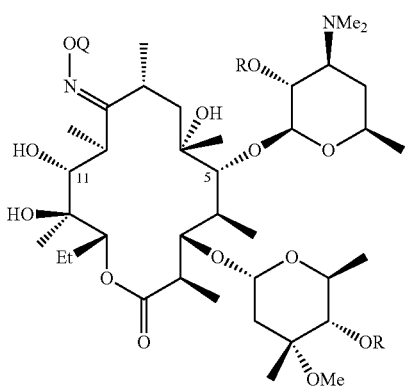

and acid addition salts thereof; wherein Q and R are as described in the various embodiments herein.

In another embodiment, compounds of formula (V) are described

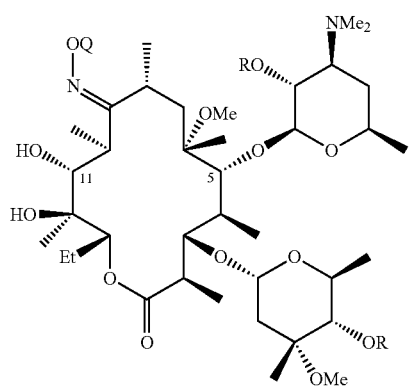

and acid addition salts thereof; wherein Q and R are as described in the various embodiments herein.

It is appreciated herein that because compounds of formulae (I), (II), (III), (IV), and (V) each contain a dimethylamino group on the desosaminyl moiety, the compounds may form acid addition salts. Accordingly, it is to be understood that any acid addition salt of a compound of formulae (I), (II), (III), (IV), and (V) suitable for use in pharmaceutical manufacturing or for providing a free base which is suitable for use in pharmaceutical manufacturing is described herein and to be included in the invention described herein.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds. For example, Illustrative crystal morphologies are described in co-pending PCT international application No. PCT/US2011/029424, the disclosure of which is incorporated herein in its entirety.

EXAMPLES

The following examples further illustrate specific embodiments of the invention; however, the following illustrative examples should not be interpreted in any way to limit the invention. Abbreviations used in the examples include the following: DCM, dichloromethane; DMAP, 4-dimethylaminopyridine; DMSO; dimethyl sulfoxide; EA, ethyl acetate; $^1$H-NMR, proton nuclear magnetic resonance spectroscopy; MeOH, methanol; Mw, molecular weight; RT, room (ambient) temperature; THF, tetrahydrofuran; TLC, thin layer chromatography.

EXAMPLE. Synthesis of erythromycin A 9-oxime (1). A mixture of erythromycin A (15 g, 20.4 mmol), $NH_2OH \cdot HCl$ (7.3 g, 105 mmol) and triethylamine (7 g, 69 mmol) in MeOH (23 mL) is heated to reflux overnight. A white solid forms during the reaction. The reaction mixture is concentrated to a small volume. To the obtained residue is added dilute aqueous $NH_4OH$ solution at 0° C. until the pH of the mixture reaches about 10 to 11. Additional solid precipitates out from the mixture. The mixture is filtered, the collected solid is washed with water and dried under vacuum to give 14.2 g of 1 as white granular solid in 93% yield. TLC analysis (DCM:MeOH: $NH_4OH$=90:10:1) of the obtained 1 shows a small amount of an additional compound (lower spot), corresponding to the Z-isomer. Mass analysis of the obtained 1 shows a peak with Mw=749, corresponding to the title compound. $^1$H-NMR analysis of the product is consistent with the title compound, and also shows a mixture of the (1) and the HCl salt thereof. The product is used without purification.

EXAMPLE. Large Scale Preparation of (1). Erythromycin (250 g, 0.34 mol) and hydroxylamine hydrochloride (80.3 g, 1.15 mol) in methanol (325 ml) are heated under reflux in the presence of triethylamine (45 g, 0.44 mol). The reaction is monitored by TLC using toluene/triethylamine (8:2) as eluent. After completion (ca. 24 h), the reaction mass is gradually cooled and stirred at 0-5° C. for 1 h, filtered and washed with cooled methanol (100 mL). The wet solid (265 g) is suspended in isopropyl alcohol (350 mL) and heated to 50-55° C. followed by the addition of aqueous ammonia (650 mL) over a period of 2 h. The solution is stirred for 1 h at 50-55° C. and gradually cooled to 10-15° C. and maintained for 2 h. The solid was filtered and washed with water and dried at 80-85° C. for 12 h to isolate 186 g. About 3% of the corresponding Z-oxime isomer is observed by HPLC. The preparation is repeated as follows with the corresponding scale of other reagents.

| No. | Batch Size | Product | Yield (%) | Purity by HPLC |
| --- | --- | --- | --- | --- |
| 1 | 100 g | 73 g | 74% | 93% + 3% of Z-oxime |
| 2 | 250 g | 186 g | 73% | 95% + 3% of Z-oxime |
| 3 | 250 g | 187 g | 73% | 95% + 3% of Z-oxime |

EXAMPLE. Synthesis of a Compound of Formula (III), Q=2-methoxy-2-propyl (9). To a solution of (1) (3 g, 4 mmol) in anhydrous dichloromethane (DCM, 21 mL) is added 2-methoxypropene (1.5 g, 20.8 mmol), followed by pyridine hydrochloride (0.72 g, 6.2 mmol) at 0° C. After the addition, the reaction mixture is stirred at 0° C. at RT for 30 min. Conversion is monitored by TLC analysis of the reaction mixture (DCM:MeOH:NH$_4$OH=90:10:1). If conversion is incomplete, the mixture is cooled back to 0° C., and another 0.5 g of 2-methoxypropene (6.9 mmol) is added. The mixture is stirred at 0° C. for another 0.5 h. If conversion is incomplete, another 0.5 g of 2-methoxypropene (6.9 mmol), followed with another 0.1 g of pyridine hydrochloride (0.86 mmol) is added to the reaction mixture at 0° C. The reaction mixture was stirred at 0° C. for another 15 min. Upon complete conversion, the reaction mixture is diluted with saturated aqueous NaHCO$_3$ solution. The DCM layer is separated and the aqueous layer is extracted with DCM. The combined DCM layers are washed with brine, dried over MgSO$_4$, concentrated to dryness to give 3.3 g crude product as a white foam in quantitative yield. Mass analysis of the product shows Mw=821, corresponding to the title compound, and a very minor peak with molecular weight of 861. $^1$H-NMR of the product is consistent with the title compound, and a small amount 2-methoxypropan-2-ol and pyridine. The product is used without further purification.

EXAMPLE. Synthesis of a Compound of Formula (IV), Q=2-methoxy-2-propyl, R=benzoyl (10). To a solution of (9) (4.1 g, 5 mmol) in ethyl acetate (65 mL) is added benzoyl anhydride (4.5 g, 20 mmol), followed by triethylamine (1.26 g, 12.5 mmol) and DMAP (0.9 g, 7.4 mmol) at RT. The resulting mixture is stirred at RT for 36 h. The reaction mixture is diluted with saturated aqueous NaHCO$_3$ solution. The EA layer is separated and the aqueous layer is extracted with EA. The combined EA layers are washed with brine, dried over MgSO$_4$, filtered to remove the drying agent, and concentrated to dryness. The obtained residue is subjected to silica gel column chromatography (DCM:MeOH: NH$_4$OH=97:3:0.3) to give 4.2 g of 10 in 80% yield as a white solid. Mass analysis of the purified product shows Mw=1029, corresponding to the title compound. $^1$H-NMR is consistent with the title compound.

EXAMPLE. Large Scale Preparation of (9). Erythromycin Oxime (1) (200 g, 026 mol) is dissolved in DCM (1.4 L) and the volume is reduced to 1 L by distillation under atmospheric pressure. After cooling the reaction mass to 0-5° C., 2-methoxypropene (80 g, 1.1 mol) and pyridine hydrobromide (50 g, 0.31 mol) are added and stirred for 3 h at 20-25° C. Mass analysis confirmed the presence of (9). Without isolation, benzoic anhydride (211 g, 0.93 mol), triethylamine (54 g, 0.53 mol), DMAP (48.8 g, 0.40 mol) are added and the reaction is continued for 24 h at 30° C. The reaction is monitored by TLC and analyzed by mass spectrometry. After completion, saturated sodium bicarbonate (1 L) is added and stirred for 15 min and allowed to settle. The layers are separated and the organic layer is concentrated. The material is isolated to 190 g with a purity of 48-51%. The preparation is repeated as follows with the corresponding scale of other reagents.

| No. | Batch Size | Unpurified Product | Purity |
| --- | --- | --- | --- |
| 1 | 200 g | 190 g | 48% |
| 2 | 200 g | 186 g | 50% |
| 3 | 200 g | 184 g | 51% |

The unpurified product from successive batches is combined (450 g) and dissolved in EA (4.5 L) to a clear solution that is washed with saturated sodium bicarbonate (2.2 L), water (2.2 L), and brine (2.2 L), and concentrated. The isolated product is crystallized from IPE/n-Hexane to 360 g (84%).

EXAMPLE. Synthesis of a Compound of Formula (V), Q=2-methoxy-2-propyl, R=benzoyl (11). A solution of (10) (3.8 g, 3.7 mmol) in anhydrous THF (15 mL) and anhydrous DMSO (15 mL) is cooled to 0° C. Powdered KOH (0.46 g, 8.2 mmol) is added, followed by methyl iodide (1.06 g, 7.5 mmol) at 0° C. The resulting reaction mixture is stirred at 0° C. for 5 min, subsequently becoming a thick paste and stopping the stirring. The mixture is warmed to RT for 5 min, remaining a thick paste, and diluted with 15 mL of THF and 15 mL of DMSO, to a free flowing suspension. The mixture is stirred at RT for another 0.5 hr, diluted with saturated aqueous NaHCO$_3$ solution, and extracted with ethyl acetate. The ethyl acetate extract is washed with brine, dried over MgSO$_4$ and concentrated to dryness. The isolated residue is purified by silica gel column chromatography (DCM:MeOH: NH$_4$OH=97:3:0.3) to 2.83 g of (11) as a white solid in 73% yield. Mass analysis shows Mw=1043), corresponding to the title compound, along with a minor peak Mw=1057. $^1$H-NMR is consistent with the title compound.

EXAMPLE. Large Scale Preparation of (11). Benzoylated oxime (10) (100 g, 0.09 mol) is dissolved in toluene (1.8 L) and the solution is distilled under vacuum to remove toluene (300 mL), cooled to 15° C., and diluted with DMSO (1.5 L). After cooling to 5° C., methyl iodide (20.5 g, 0.14 mol) is added followed by KOH (10.8 g, 0.19 mol) and the reaction is continued for 3 h. The reaction is stopped by the addition of 40% dimethylamine (22 g) and the temperature of the reaction mass is raised to RT and diluted with water (500 mL) with stirring. The layers are separated and the aqueous layer is extracted with toluene (500 mL). The combined organic layers are washed with water (2 L) and the organic layer is concentrated by distillation under vacuum. The isolated product is stirred in IPE (500 mL) for 5 h and filtered to 82 g of the title compound, which is used without further purification. The preparation is repeated as follows with the corresponding scale of other reagents.

| No. | Batch Size | Product | Yield (%) |
| --- | --- | --- | --- |
| 1 | 100 g | 82 g | — |
| 2 | 100 g | 78 g | — |
| 3 | 100 g | 84 g | — |
| 4 | 90 g | 71 g | 80% |

EXAMPLE. Synthesis of a Clarithromycin Dibenzoate, Formula (II), R=benzoyl. To a solution of (11) (800 mg, 0.78 mmol) in ethanol (8 mL) and water (8 mL) is added sodium metabisulfite (740 mg, 3.89 mmol) at RT. The resulting mixture is adjusted to pH 2-3 by adding formic acid (1.5 mL). The mixture is heated at 60° C. for 1 h. Conversion is monitored by mass spectrometry. If incomplete, or showing a large amount of the deprotected oxime intermediate (Mw=971), another 2 g of sodium metabisulfite (10.5 mmol) is added. The mixture is stirred at 60° C. for another 7 h, then cooled to RT. A white solid precipitate forms as the reaction progresses. The reaction mixture is neutralized with dilute aqueous NaHCO₃ solution to pH of 8-9 and the resulting mixture is filtered. The isolated white solid is dried under vacuum to 760 mg of clarithromycin dibenzoate. The unpurified product is combined with material obtained from other preparations (ca. 200 mg) and purified by silica gel column chromatography to 730 mg of clarithromycin dibenzoate in 79% yield. Mass analysis shows Mw=956, corresponding to the title compound, with a minor peak of Mw=970, which is attributed to the carryover impurity in (11). $^1$H-NMR is consistent with the title compound.

EXAMPLE. Large Scale Preparation of Clarithromycin Dibenzoate. Methylated oxime (11) (80 g, 0.07 mol) is dissolved in absolute alcohol (400 mL). Water (400 mL) is added, followed by sodium bisulfite (72 g, 0.69 mol) and formic acid (21 g). The reaction mass is heated to reflux for 6 h, cooled to RT, and diluted with water (400 mL). The reaction mass is cooled to 10-15° C., and 25% NaOH (160 ml) is added slowly. The mixture is stirred for 2 h and filtered. The isolated solid is washed with water (500 mL) and dissolved in ethylacetate (400 mL). The organic layer is washed with water (400 mL), then brine (400 mL), then concentrated. The isolated material is crystallized from ethyl acetate (1.7 T) to 40.8 g (95% purity). Alternatively, the isolated material is crystallized from IPA/IPE 89-90% purity. The preparation is repeated as follows with the corresponding scale of other reagents.

| No. | Batch Size | Product | Yield (%) |
|-----|-----------|---------|-----------|
| 1   | 80 g      | 40.8 g  | 95%       |
| 2   | 70 g      | 37.8 g  | 90%       |
| 3   | 70 g      | 45 g    | 89%       |

What is claimed is:

1. A process comprising (a) the step of contacting a compound of formula (III)

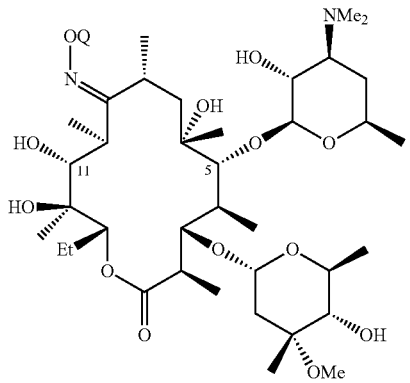

(III)

or a salt thereof, wherein Q in combination with the oxime oxygen forms an acetal or ketal, with an acylating agent to form a compound of formula (IV)

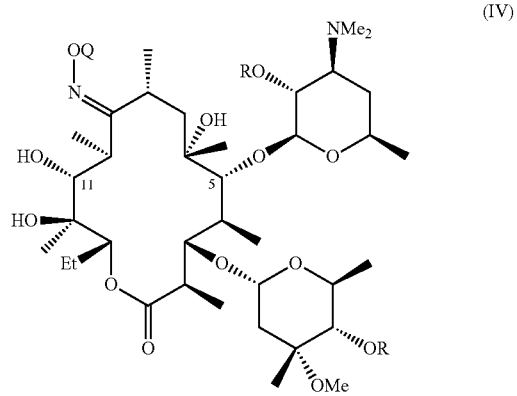

(IV)

or a salt thereof, wherein R is an acyl group; or
(b) the step of contacting a compound of formula (IV), or a salt thereof, with a methylating agent, to form a compound of formula (V)

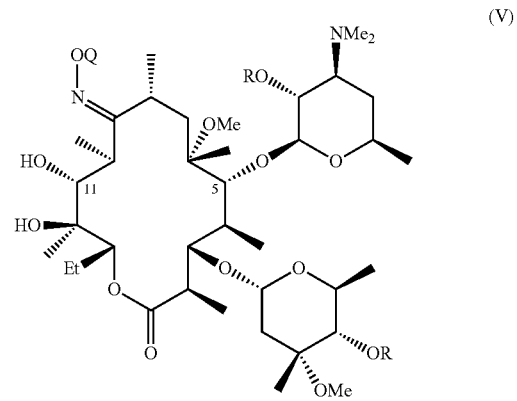

(V)

or a salt thereof; or
(c) the step of contacting a compound of formula (V), or a salt thereof, with a deoximating agent to form a compound of formula (II)

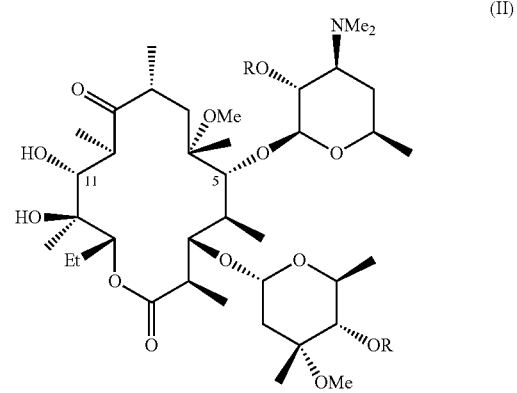

(II)

or a salt thereof; or
(d) any combination of (a), (b), and (c).

2. The process of claim 1 comprising (a) and (b).
3. The process of claim 1 comprising (a) and (c).
4. The process of claim 1 comprising (b) and (c).
5. The process of claim 1 comprising (a), (b), and (c).
6. A process for preparing a compound of formula (II)

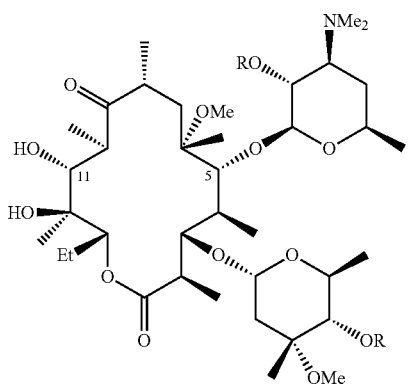

(II)

or a salt thereof, wherein:
R is an acyl group;
the process comprising (c) the step of contacting a compound of formula (V)

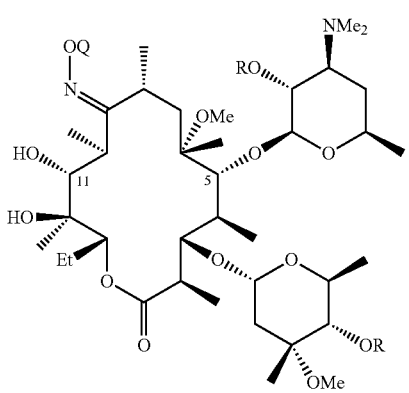

(V)

or a salt thereof, with a deoximating agent to form the compound of formula (II).

7. The process of claim 6 further comprising (b) the step of contacting a compound of formula (IV)

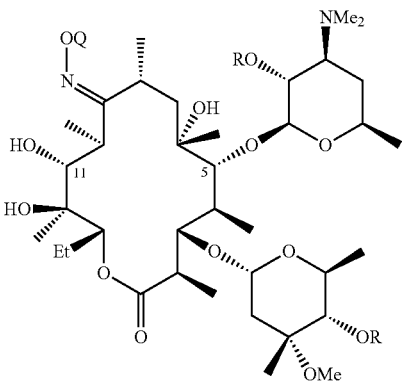

(IV)

or a salt thereof, wherein R is an acyl group, with a methylating agent, to form a compound of formula (V)

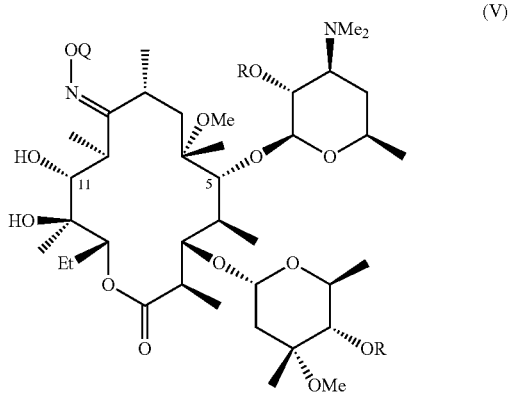

(V)

or a salt thereof.

8. The process of claim 7 further comprising (a) the step of contacting a compound of formula (III)

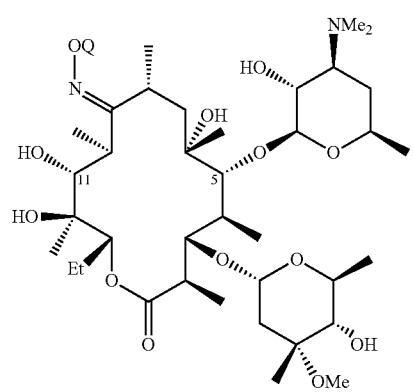

(III)

or a salt thereof, wherein Q in combination with the oxime oxygen forms an acetal or ketal, with an acylating agent to form a compound of formula (IV)

(IV)

or a salt thereof, wherein R is an acyl group.

9. The process of claim 6 comprising (a) the step of contacting a compound of formula (III)

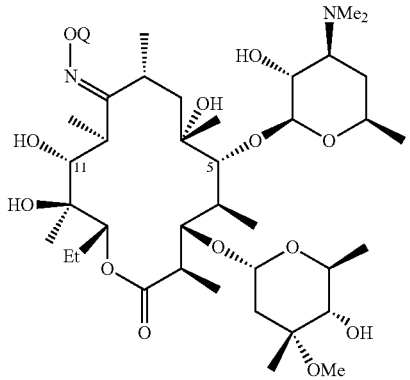

(III)

or a salt thereof, wherein Q in combination with the oxime oxygen forms an acetal or ketal, with an acylating agent to form a compound of formula (IV)

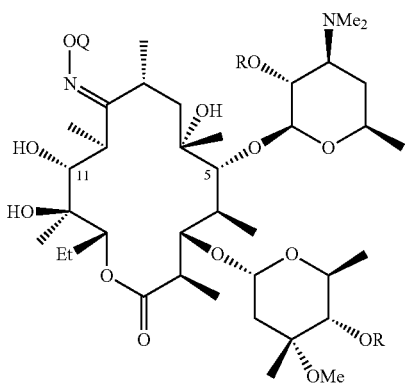

(IV)

or a salt thereof, wherein R is an acyl group(b) and (c).

10. A compound of formula (IV) or (V)

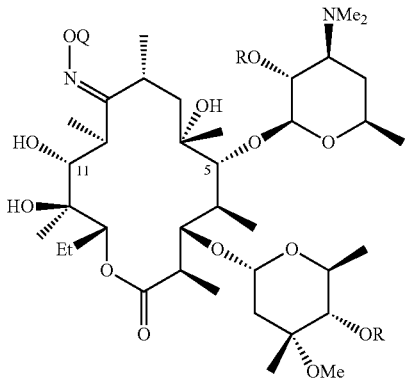

(IV)

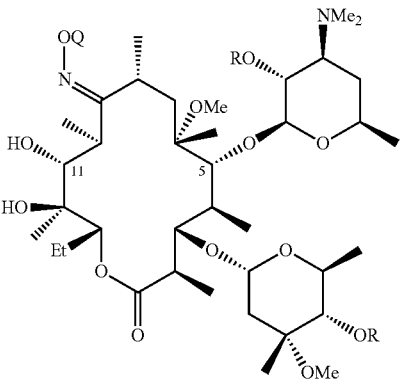

(V)

or an acid addition salt thereof, wherein Q in combination with the oxime oxygen forms an acetal or ketal, and R is an acyl group.

11. The compound of claim 10 wherein Q is 2-methoxy-2-propyl, 1-methoxycyclohexyl or 1-isopropoxycyclohexyl.

12. The compound of claim 10 wherein Q is 2-methoxy-2-propyl.

13. The compound of claim 10 wherein R is a sterically hindered acyl group.

14. The compound of claim 10 wherein R is benzoyl.

15. The process of claim 1 wherein the acylating agent is the anhydride.

16. The process of claim 1 wherein the methylating agent in step (b) is methyl bromide, methyl iodide, dimethyl sulfate, methyl p-toluenesulfonate or methyl methanesulfonate.

17. The process of claim 1 wherein the deoximating agent in step (c) comprises a reducing agent.

18. The process of claim 1 wherein the deoximating agent in step (c) comprises formic acid and sodium metabisulfite.

19. The process of claim 1 wherein Q is 2-methoxy-2-propyl, 1-methoxycyclohexyl or 1-isopropoxycyclohexyl.

20. The process of claim 1 wherein Q is 2-methoxy-2-propyl.

21. The process of claim 1 wherein R is benzoyl.

22. The process of claim 6 wherein the acylating agent is the anhydride.

23. The process of claim 6 wherein the methylating agent in step (b) is methyl bromide, methyl iodide, dimethyl sulfate, methyl p-toluenesulfonate or methyl methanesulfonate.

24. The process of claim 6 wherein the deoximating agent in step (c) comprises formic acid and sodium metabisulfite.

25. The process of claim 6 wherein Q is 2-methoxy-2-propyl, 1-methoxycyclohexyl or 1-isopropoxycyclohexyl.

26. The process of claim 6 wherein Q is 2-methoxy-2-propyl.

27. The process of claim 6 wherein R is benzoyl.

28. The compound of claim 10 of formula (IV), or a salt thereof.

29. The compound of claim 28 wherein Q is 2-methoxy-2-propyl.

30. The compound of claim 28 wherein R is benzoyl.

31. The compound of claim 28 wherein Q is 2-methoxy-2-propyl, 1-methoxycyclohexyl or 1-isopropoxycyclohexyl; and R is benzoyl.

32. The compound of claim 10 of formula (V), or a salt thereof.

33. The compound of claim 32 wherein Q is 2-methoxy-2-propyl.

34. The compound of claim 32 wherein R is benzoyl.

35. The compound of claim 32 wherein Q is 2-methoxy-2-propyl, 1-methoxycyclohexyl or 1-isopropoxycyclohexyl; and R is benzoyl.

\* \* \* \* \*

UNITED STATES PATENT AND TRADEMARK OFFICE
CERTIFICATE OF CORRECTION

PATENT NO. : 9,051,346 B2
APPLICATION NO. : 13/699020
DATED : June 9, 2015
INVENTOR(S) : David E. Pereira Page 1 of 1

It is certified that error appears in the above-identified patent and that said Letters Patent is hereby corrected as shown below:

In the claims,

In claim 9, column 19, line 47, "or a salt thereof, wherein R is an acyl group(b) and (c)." should read -or a salt thereof, wherein R is an acyl group.-

Signed and Sealed this
Sixth Day of October, 2015

Michelle K. Lee
*Director of the United States Patent and Trademark Office*